(12) United States Patent
Fontana

(10) Patent No.: US 8,662,780 B2
(45) Date of Patent: Mar. 4, 2014

(54) CONTAINER FOR FLUID PRODUCTS, PARTICULARLY CREAMS, OINTMENTS, PASTES, LOTIONS FOR MEDICAL, PHARMACEUTICAL OR COSMETIC USE

(75) Inventor: Antonio Fontana, Carpi (IT)

(73) Assignee: Lameplast S.P.A., Frazione Robereto sul Secchia (MO) (IT)

( * ) Notice: Subject to any disclaimer, the term of this patent is extended or adjusted under 35 U.S.C. 154(b) by 624 days.

(21) Appl. No.: 12/995,719

(22) PCT Filed: May 25, 2009

(86) PCT No.: PCT/IB2009/005709
§ 371 (c)(1),
(2), (4) Date: Dec. 2, 2010

(87) PCT Pub. No.: WO2009/147484
PCT Pub. Date: Dec. 10, 2009

(65) Prior Publication Data
US 2011/0082432 A1    Apr. 7, 2011

(30) Foreign Application Priority Data

Jun. 4, 2008 (IT) .............................. MO2008A0171

(51) Int. Cl.
*B05C 11/00* (2006.01)

(52) U.S. Cl.
USPC ............ 401/266; 401/262; 401/183; 401/132

(58) Field of Classification Search
USPC .................. 401/261–266, 183–186, 132–134
See application file for complete search history.

(56) References Cited

U.S. PATENT DOCUMENTS

| | | | | |
|---|---|---|---|---|
| 2,550,132 | A * | 4/1951 | Woods .......................... | 222/490 |
| 2,716,251 | A * | 8/1955 | Pearce .......................... | 401/139 |
| 2,930,063 | A * | 3/1960 | Stull ............................. | 401/132 |
| 2,982,987 | A * | 5/1961 | Knapp .......................... | 401/139 |
| 3,090,071 | A * | 5/1963 | Le Brooy ..................... | 401/266 |
| 4,738,379 | A   | 4/1988 | Takasugi | |
| 4,990,016 | A   | 2/1991 | Seidler | |
| 5,902,060 | A * | 5/1999 | Rodriguez ................... | 401/1 |
| 6,343,717 | B1  | 2/2002 | Zhang | |
| 7,465,118 | B2 * | 12/2008 | Liberatore .................. | 401/266 |
| 8,475,072 | B1 * | 7/2013 | Buckner et al. ............. | 401/261 |

FOREIGN PATENT DOCUMENTS

| | | |
|---|---|---|
| GB | 2 390 362 | 1/2004 |
| WO | WO 2007/107826 | 9/2007 |

* cited by examiner

*Primary Examiner* — David Walczak
(74) *Attorney, Agent, or Firm* — Stein IP, LLC

(57) ABSTRACT

The container for fluid products, particularly creams, ointments, pastes, lotions for medical, pharmaceutical or cosmetic use, comprises a containment body for containing a fluid product which has an exit mouth for the fluid product, a closing element for closing the mouth, and an applicator element associable with the containment body near to the mouth and suitable for dispensing the fluid product exiting from the mouth.

4 Claims, 3 Drawing Sheets

Fig. 1
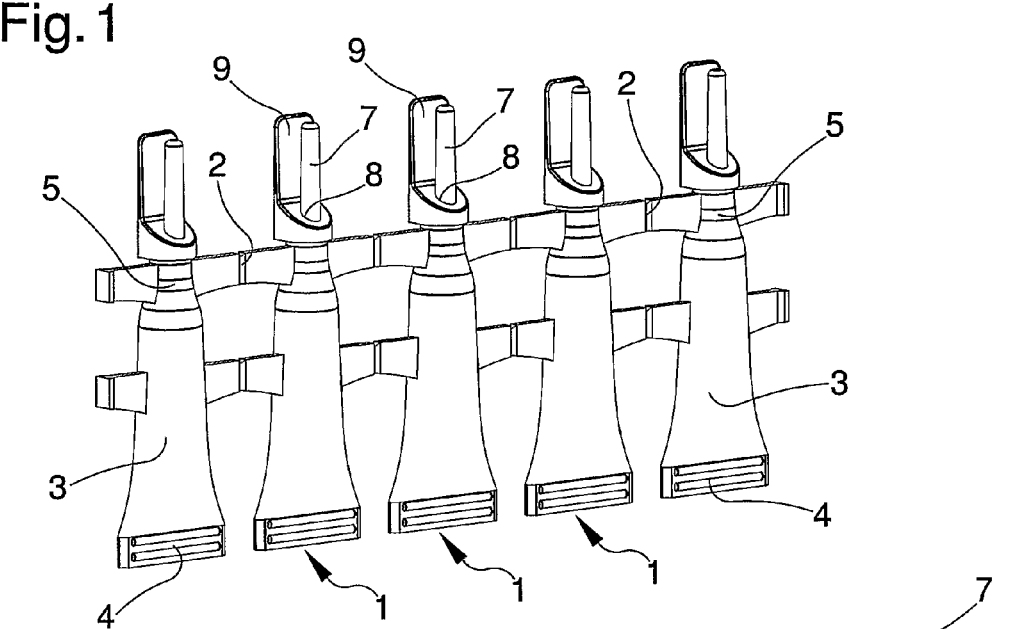
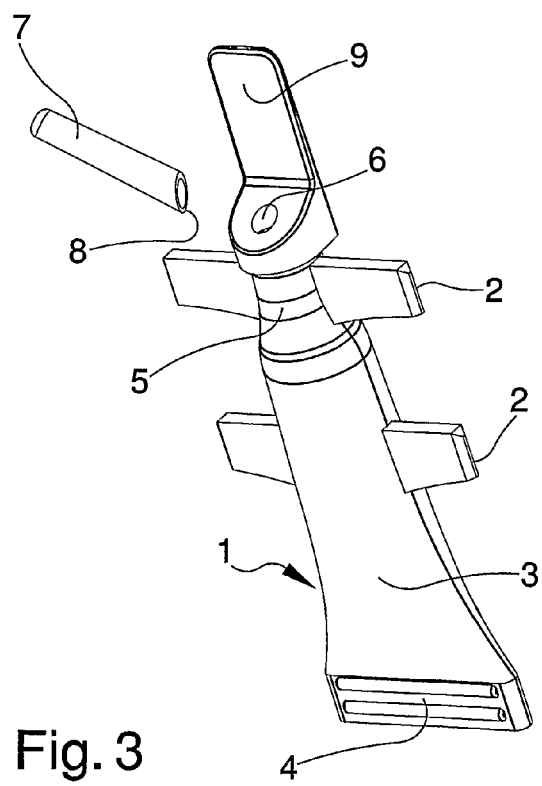
Fig. 3
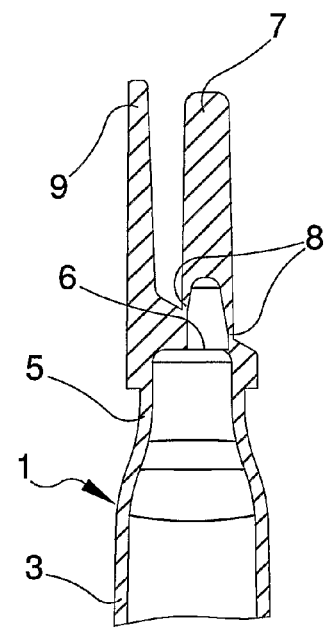
Fig. 2

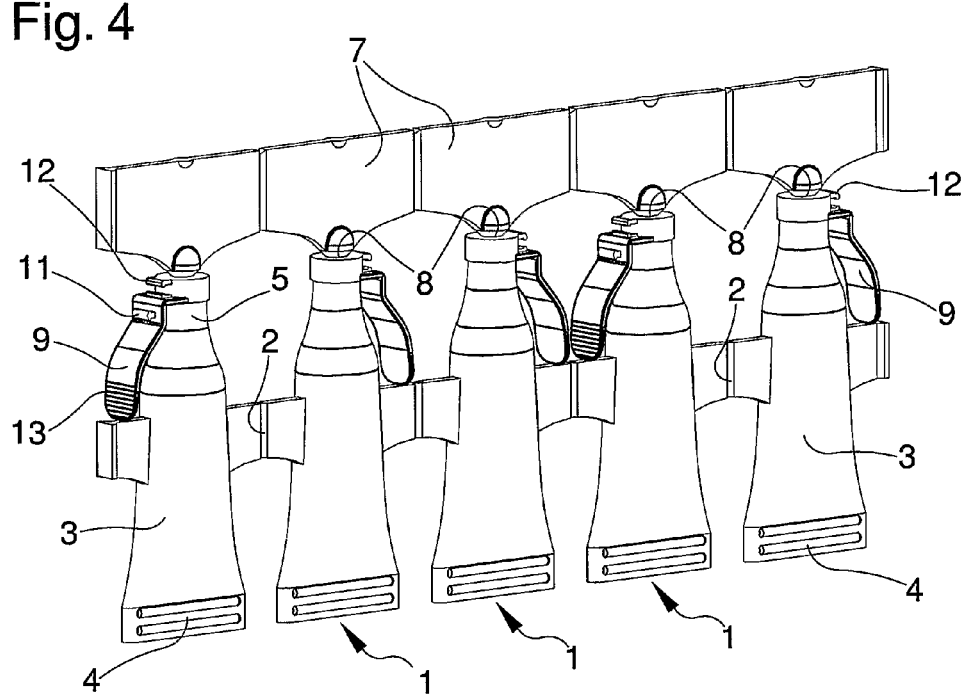
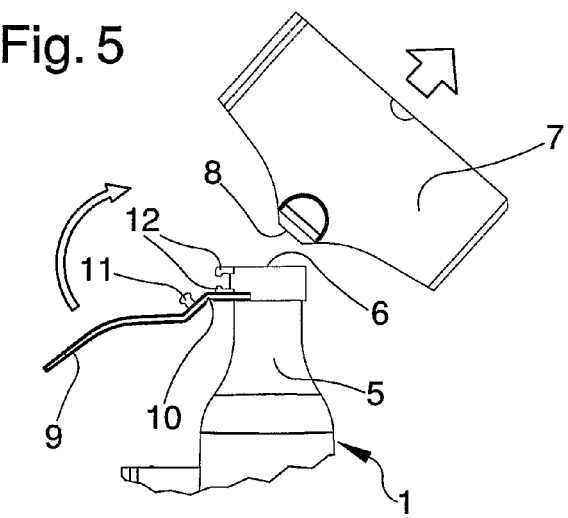
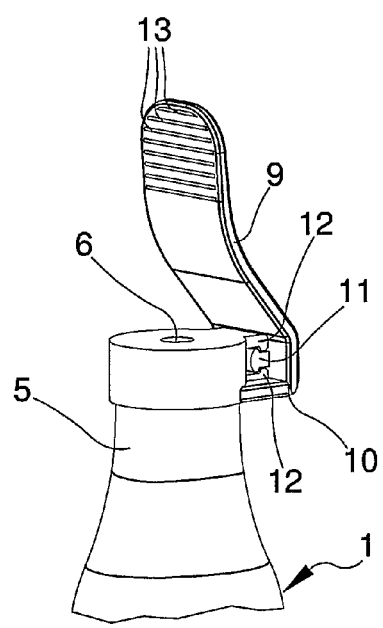

CONTAINER FOR FLUID PRODUCTS, PARTICULARLY CREAMS, OINTMENTS, PASTES, LOTIONS FOR MEDICAL, PHARMACEUTICAL OR COSMETIC USE

CROSS-REFERENCE TO RELATED APPLICATIONS

This application claims the benefit of PCT International Patent Application No. PCT/IB2009/005709, filed May 25, 2009, and Italian Patent Application No. MO2008A000171, filed Jun. 4, 2008, in the Italian Patent and Trademark Office, the disclosures of which are incorporated herein by reference.

BACKGROUND OF THE INVENTION

1. Field of the Invention

The present invention relates to a container for fluid products, particularly creams, ointments, pastes, lotions for medical, pharmaceutical or cosmetic use.

2. Description of the Related Art

It is known that for the application of particular cosmetic products such as nail enamels, poultices, foundation creams and other fluid substances, small bottles are usually used made of glass or other material containing the product and which have an opening onto which a closing cap can be screwed.

With the closing cap is usually associated a rod supporting a small brush for spreading the product on the nails and/or on the parts of the body to be covered with the product.

These containers of known type have a number of drawbacks, including the fact that they are usually fairly heavy and cumbersome and are not very practical and easy to use because they require the use of both hands, one to hold the bottle tight and the other to grip the brush and spread the product to be applied.

This means a considerable waste of time and less practical use for the user.

Patent documents U.S. Pat. Nos. 4,990,016, 6,343,717 B1 and GB 2 390 362 A disclose various embodiments of containers for dispensing fluid substances, and corresponding uses.

However even these known embodiments appear to require further improvements in particular when the dispensed fluid product has to be spread on a surface, so as in particular to allow a user to dose in a practical and convenient way the amount of the dispensed fluid product intended to be spread.

SUMMARY OF THE INVENTION

The main aim of the present invention is to provide a container for fluid products, particularly creams, ointments, pastes, lotions for medical, pharmaceutical or cosmetic use, that is particularly lightweight and small, practical, easy and functional to use, can be opened quickly using just one hand, freeing the user from the need of having to use both hands.

Another object of the present invention is to provide a container for fluid products, particularly creams, ointments, pastes, lotions for medical, pharmaceutical or cosmetic use, that overcomes the mentioned drawbacks of the background art in the ambit of a simple, rational, easy, effective to use and low cost solution.

The above objects are achieved by the present container for fluid products, particularly creams, ointments, pastes, lotions for medical, pharmaceutical or cosmetic use, having all the features recited by the main independent claim 1.

BRIEF DESCRIPTION OF THE DRAWINGS

Other characteristics and advantages of the present invention will become more evident from the description of some forms of preferred, but not sole, embodiments, of a container for fluid products, particularly creams, ointments, pastes, lotions for medical, pharmaceutical or cosmetic use, illustrated purely as an example but not limited to the annexed drawings in which:

FIG. 1 is an axonometric view of a first embodiment of the container according to the invention in a closing configuration;

FIG. 2 is a section view of a portion of the container of FIG. 1;

FIG. 3 is an axonometric view of the container of FIG. 1 in an opening configuration;

FIG. 4 is an axonometric view of a second embodiment of the container according to the invention in an idle configuration;

FIG. 5 is a front, schematic and partial view of the container of FIG. 4 in the passage from idle configuration to operating configuration;

FIG. 6 is an axonometric, schematic and partial view of the container of FIG. 4 in the operating configuration;

DETAILED DESCRIPTION OF THE EMBODIMENTS

Figure 10:
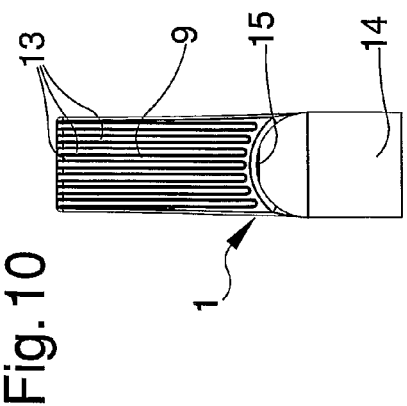
FIG. 10 is a front view of the applicator element as per the fourth embodiment of the invention.

With particular reference to the form of embodiment of the invention shown in the FIGS. from 1 to 3, a container for fluid products, particularly creams, ointments, pastes, lotions for medical, pharmaceutical or cosmetic use, has been globally indicated by 1.

Usefully, the container 1 is of the disposable type and can be mass produced to make up strips of several pieces, each joined together by means of connectors 2.

As shown in FIG. 1, connectors 2 are defined by connection tabs joined along weakened temporary connection sections.

Each container 1 comprises a containment body 3 suitable for containing a fluid product of the cream, poultice, nail enamel, foundation cream type, etc.

The containment body 3 has a bottom 4 and an elongated neck 5 which is arranged on side opposite to the bottom 4 and which has a mouth 6 for the fluid product to exit.

Furthermore, the containment body 3 is made of at least partially compressible material to allow the fluid product to exit through the mouth 6.

This material is, e.g., plastic modelled by injection moulding or the like.

With the neck 5 is associated a closing element 7 for keeping the mouth 6 closed until it is necessary for the fluid product to exit.

Usefully, the containment body 3 and the closing element 7 are made in a single body piece and can be separated by tearing.

In this respect, the closing element 7 is composed of an elongated grip pin, which is connected to the mouth 6 along an edge 8 with a weakened section which can be torn before use.

With the containment body 3 is associated an applicator element 9 positioned close to the mouth 6 and suitable for dispensing the fluid product exiting through the mouth 6.

In this respect, it must be specified that when it is stated that the applicator element 9 allows dispensing the fluid product, it is meant that it is possible to use the applicator to apply, spread, lay, cover, brush or perform similar operations.

Usefully, in the embodiment shown in the FIGS. from 1 to 3, the applicator element 9 consists of a spatula intended for spreading the fluid product on the skin, on the nails and/or, more generally, on any surface of the user's body.

Alternative embodiments of the invention cannot, however, be ruled out in which the applicator element 9 has a different shape and, consists in a bristly head, a brush, a comb or the like.

The spatula is made in a single body piece with the containment body 3 and has a portion that is substantially flat and smooth on the surface. The spatula is rigidly associated with the containment body 3 alongside the pin 7 and in the path of exit of the fluid product from the mouth 6.

This way, just as soon as the pin 7 is torn away, the fluid product can be dispensed through the mouth 6 by simply squeezing the containment body 3.

The exiting fluid product is discharged directly on the spatula element 9 with which it can be spread by the user in the way that suits him/her best.

In the embodiment shown in the FIGS. from 4 to 6, the container 1 has a containment body 3 having a bottom 4 and a mouth 6 substantially the same as those of the previous embodiment and which, therefore, will not be the subject of any detailed further explanation, its being understood that for these it is best to refer to the above description.

In the embodiment shown in the FIGS. from 4 to 6 as well, the mouth 6 is closed with a closing element 7 obtained in a single body piece with the containment body 3 and removable by tearing, with the difference however, that it is composed of a plate-shaped grip body, connected to the mouth 6 along an edge 8 with weakened section.

In this embodiment as well, the container 1 has an applicator element 9 of the type of a spatula element which, unlike the above, is defined by a substantially flattened portion associated with the neck 5 in a rotatable manner. The applicator may be pivoted between an idle configuration (FIG. 4), in which the spatula is arranged substantially alongside the containment body 3, and an operating configuration (FIG. 6), in which the spatula is arranged substantially along the exit direction of the fluid product from the mouth 6.

For this purpose, it is pointed out that the spatula is obtained in a single body piece with the neck 5 and joined to this along a connecting line 10 with a weakened section, which allows it to be hinged between the idle configuration and the operating configuration.

The container 1 also has retention means 11, 12 suitable for securing the spatula in the operating configuration.

These retention means are defined by a first interlocking tooth 11, which is associated with the spatula and can be coupled by interlocking engagement between a pair of interlocking teeth 12, that are located upon the neck 5 of the containment body 3.

Advantageously, in this embodiment, the spatula has a series of enlarged relief surfaces defined a direction at right angles to the exit direction of the fluid product from the mouth 6, and making it easier to spread by the user.

Alternatively to the embodiments previously described and shown, different embodiments are possible in which the containment body 3 and the applicator element 9 are made separately from one another, and can be joined before use.

Figure 7:
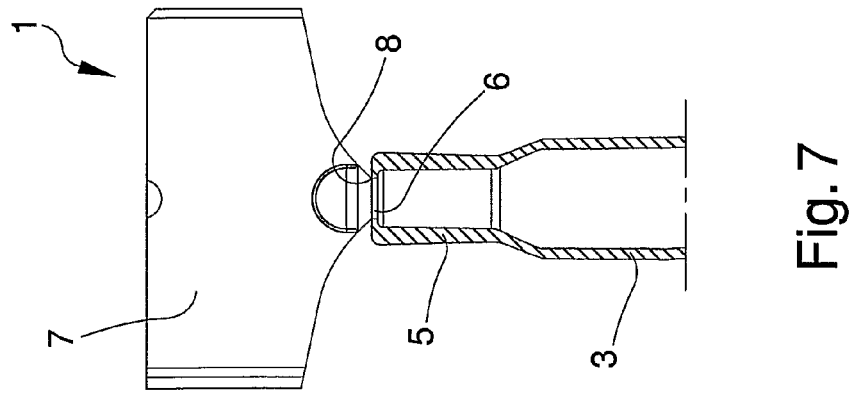
FIG. 7 is a section view of a portion of the container as per a third and fourth embodiment of the invention.

In these particular embodiments, the containment body 3 and the closing element 7 make up an element in itself, independent from the applicator element 9, e.g., as shown in the FIG. 7 in which the containment body 3 and the closing element 7 are substantially similar to those of the embodiment in the figures from 4 to 6, with the closing element 7 made up of a plate-shaped grip body removable by tearing from the mouth 6.

That the closing element 7 can have shapes and dimensions different from those shown in FIG. 7 cannot however be ruled out.

The applicator element 9, on the other hand, comprises a cap 14 which is fitted for use by interlocking on the neck 5 after the closing element 7 has been removed from the mouth 6.

The cap 14 does not stop the fluid product from exiting inasmuch for it has a transit opening 15, which in the use configuration, is arranged substantially aligned and coinciding with the mouth 6.

Furthermore, the applicator element 9 comprises a spatula having a substantially flattened portion associated with the cap 14 which, in the use configuration, is arranged substantially along the exit direction of the fluid product discharged from mouth 6.

Figure 11:
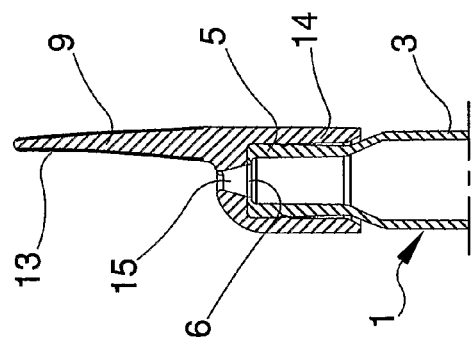
FIG. 11 is a section, schematic and partial view of the applicator element of FIG. 10 in a use configuration.
Figure 8:
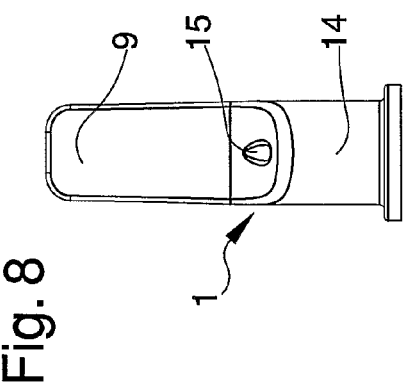
FIG. 8 is a front view of the applicator element as per the third embodiment of the invention.
Figure 9:
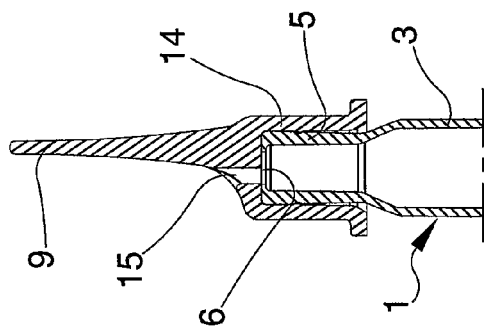
FIG. 9 is a section, schematic and partial view of the applicator element of FIG. 8 in a use configuration.

The FIGS. 8 and 9, show a third embodiment of the invention in which the applicator element 9 is substantially smooth while, the FIGS. 10 and 11 show a fourth embodiment in which, on the other hand, the applicator element 9 has a series of surface reliefs 13 suitable for making it easier to spread the fluid product and elongated along a direction substantially parallel to the exit direction of the fluid product from the mouth 6.

Both for the embodiment of the FIGS. 8 and 9 and for the embodiment of the FIGS. 10 and 11, the containment body 3 is distributed or sold in the market place separate from the applicator element 9.

In this respect, it is pointed out that each container 1 can be distributed with a corresponding cap 14 intended to be used only with one containment body 3 and to be thrown away with this after use.

Alternatively, each pack of containers 1 can contain a plurality of containment bodies 3, closed by respective closing elements 7, and just one cap 14 which can be recycled after each use and can be used with all the containment bodies 3.

It has in point of fact been ascertained how the described invention achieves the proposed objects.

The invention thus conceived is susceptible to numerous modifications and variations, all of which fall within the scope of the inventive concept.

Furthermore all the details can be replaced with others that are technically equivalent.

In practice, the materials used, as well as the contingent shapes and dimensions, may be any according to requirements without because of this moving outside the protection scope of the following claims. Thus, the appended claims should be broadly construed, and should not be limited to their literal terms.

The invention claimed is:

1. A container for fluid products, particularly creams, pastes, lotions for medical, pharmaceutical or cosmetic use, said container comprising:
  1) a containment body for retaining a fluid product, 2) said body being closed at one end and including an elongated neck with an exit mouth at the end remote from said closed end to allow the fluid product to exit,
3) a closing element for sealing said exit mouth,
4) said closing element joined to said containment body along a tear line,
5) a spatula joined to said containment body adjacent to said exit mouth in said containment body,
6) said containment body, said spatula, and said closing element being formed as a single body piece,
7) said closing element being torn away from said containment body along a scored line to open said exit mouth and expose the contents of said containment body,
8) said containment body being formed of a partially compressible material for discharging said fluid product through said exit mouth, whereby
9) squeezing said containment body discharges fluid product through said mouth directly onto said spatula for spreading by a user of the container.

2. The container as defined in claim 1 wherein said containment body extends in a longitudinal direction from said closed end to said exit mouth in said elongated neck.

3. The container of claim 2 wherein said closing element is a grip pin, said grip pin extending away from said containment body in a longitudinal plane parallel to said spatula.

4. The container as defined in claim 1 wherein said spatula includes a relief surface for making said fluid product easier to spread.

* * * * *